US007629005B2

(12) United States Patent
Popp

(10) Patent No.: US 7,629,005 B2
(45) Date of Patent: Dec. 8, 2009

(54) PHARMACEUTICAL FORMULATION CONSISTING OF A PLANT DRY EXTRACT WITH A CALCIUM COATING

(75) Inventor: Michael A. Popp, Nuemarkt (DE)

(73) Assignee: Bionorica AG, Neumarkt (DE)

( * ) Notice: Subject to any disclaimer, the term of this patent is extended or adjusted under 35 U.S.C. 154(b) by 0 days.

(21) Appl. No.: 10/480,078

(22) PCT Filed: Apr. 10, 2002

(86) PCT No.: PCT/EP02/04002

§ 371 (c)(1), (2), (4) Date: Dec. 8, 2003

(87) PCT Pub. No.: WO02/100422

PCT Pub. Date: Dec. 19, 2002

(65) Prior Publication Data

US 2004/0151781 A1 Aug. 5, 2004

(30) Foreign Application Priority Data

Jun. 8, 2001 (DE) ................................ 101 27 897

(51) Int. Cl.
- A61K 36/00 (2006.01)
- A61K 36/48 (2006.01)
- A61K 36/42 (2006.01)

(52) U.S. Cl. .................... 424/725; 424/757; 424/758
(58) Field of Classification Search ................. 424/439, 424/474, 602, 725, 727, 757, 758; 514/769, 514/960
See application file for complete search history.

(56) References Cited

U.S. PATENT DOCUMENTS

| | | | |
|---|---|---|---|
| 2,410,417 A * | 11/1946 | Andersen | 424/459 |
| 3,030,273 A * | 4/1962 | Zagnoli | 424/477 |
| 4,681,766 A | 7/1987 | Huzinec et al. | |
| 4,752,479 A | 6/1988 | Briggs et al. | |
| 4,915,948 A * | 4/1990 | Gallopo et al. | 424/435 |
| 4,996,061 A * | 2/1991 | Webb et al. | 424/475 |
| 5,093,130 A * | 3/1992 | Fujii et al. | 424/463 |
| 5,569,456 A | 10/1996 | Gorinsky | |
| 5,569,459 A | 10/1996 | Shlyankevich | |
| 5,948,443 A * | 9/1999 | Riley et al. | 424/643 |
| 6,004,558 A * | 12/1999 | Thurn et al. | 424/757 |
| 6,139,872 A * | 10/2000 | Walsh | 424/464 |
| 6,200,594 B1 * | 3/2001 | Ernest et al. | 424/439 |
| 6,264,985 B1 | 7/2001 | Cremer | |
| 6,267,994 B1 * | 7/2001 | Nesselhut et al. | 424/773 |
| 6,444,218 B2 | 9/2002 | Han et al. | |
| 2001/0036468 A1 | 11/2001 | Han et al. | |
| 2004/0151781 A1 | 8/2004 | Popp | |
| 2007/0122503 A1 | 5/2007 | Wuttke et al. | |

FOREIGN PATENT DOCUMENTS

| | | |
|---|---|---|
| CN | 1179972 A | 4/1998 |
| DE | 3717543 A1 | 12/1987 |
| DE | 4431653 A1 | 3/1996 |
| DE | 19814905 A1 | 10/1999 |
| DE | 19812204 A1 | 11/1999 |
| EP | 1 392 337 B1 | 11/2005 |
| JP | 62224244 A | 10/1987 |
| JP | 09030977 A * | 2/1997 |
| JP | 2001506541 A | 5/2001 |
| KR | 267 576 B | 2/2000 |
| KR | 267576 B | 2/2000 |
| RU | 2000 126476 A | 8/2002 |
| RU | 2 196 601 C2 | 1/2003 |
| WO | 9912640 | 3/1999 |
| WO | 9947149 | 9/1999 |
| WO | 0000177 | 1/2000 |
| WO | 00/06127 | 2/2000 |
| WO | WO 00 30605 A | 2/2000 |
| WO | 0020015 | 4/2000 |
| WO | WO 0028973 A1 * | 5/2000 |
| WO | 00/30605 | 6/2000 |

(Continued)

OTHER PUBLICATIONS

Solid Dosage Forms- Tablets & Capsules [online] Jan. 7, 2000 [retrieved on Sep. 22, 2007]. Retrived from the Internet: <http://web.archive.org/web/*/http://pharmacy.wilkes.edu/kibbeweb/lect14.html>.*

(Continued)

*Primary Examiner*—Christopher R Tate
*Assistant Examiner*—Amy L Clark
(74) *Attorney, Agent, or Firm*—Patent Central LLC; Stephan A. Pendorf

(57) ABSTRACT

A pharmaceutical formulation of a calcium salt and a dry plant extract in the form of a coated tablet, in which the formulation has a core of at least one dry plant extract, enveloped by at least one coating of at least one calcium salt. The plant extracts for the core may be selected from: *Vitex agnus castus* (chaste tree); *Belamcanda chinensis* (leopard lily); *Cimicifuga racemosa* (black cohosh); *Trifolium pratense L.* (purple trefoil); *Oenothera biennis hom.* (primrose); *Glycine soja* (soy bean); *Serenoa repens* (saw-palmetto); *Urtica dioica* (stinging nettle), in particular its root; *Cucurbita pepo* (pumpkin), in particular its seed; *Pygeum africanum*; as well as suitable mixtures of these. Methods for the use of the formulation in treating osteoporosis and for manufacturing the formulation are provided.

5 Claims, No Drawings

FOREIGN PATENT DOCUMENTS

| | | |
|---|---|---|
| WO | WO 00/30605 | 6/2000 |
| WO | WO 02/100422 A1 | 12/2002 |

OTHER PUBLICATIONS capsule-Synonyms from Thesaurus.com (U, http://thesaurus.reference.co/browse/capsule.*

Solid Dosage Forms—Tablets & Capsules Jan. 17, 2000 [Retrieved from the Internet on: Sep. 22, 2007]. Retrieved from http://web.archive.org/web/*/http://pharmacy.wilkes.edu/kibbeweb/lect14.html.*

Prince, et al., "What strategies can women use to optimise bone health at this stage of life?", Med J Aust., 173 Suppl: S106-7 (2000).

* cited by examiner

_US 7,629,005 B2_

PHARMACEUTICAL FORMULATION CONSISTING OF A PLANT DRY EXTRACT WITH A CALCIUM COATING

CROSS REFERENCE TO RELATED APPLICATION

This application is a national stage of PCT/EP02/04002 filed Apr. 10, 2002 and based upon DE 101 27 897.7-41 filed Jun. 8, 2001 under the International Convention.

FIELD OF THE INVENTION

The present invention relates to a pharmaceutical formulation in the form of a coated tablet, wherein the coating is a pressed body of at least one calcium salt, and the core is a pressed body of at least one of the named dry plant extracts, wherein vitamin $D_3$ may in addition be contained in the core, a use thereof and a method for its manufacture.

BACKGROUND TO THE INVENTION

17β-estradiol, which is naturally formed in the ovaries [also referred to as $E_2$], has a general proliferation-enhancing action in humans and animals. In addition to controlling the female cycle, it has, i.a., a homeostatic effect on the metabolism of the bone, while also preventing the formation of atherotic plaques on vessel endothelia.

During menopause, estradiol levels decrease due to cessation of ovarial function. In the absence of sufficiently high estradiol levels in the blood, the activity of the osteoclasts, and thus breakdown of the bone mass—so-called "osteoporosis"—predominates in the bone tissue, which is accompanied by an increased risk of skeletal breakage.

In recent times it was found that this syndrome of osteoporosis brought about by lack of sexual hormone is not restricted to women, but that from a certain advanced age, osteoporosis brought about by lack of sexual hormone also occurs in men, in particular in connection with ailments of the prostate.

The classical prophylaxis and therapy in woman consists in supplementing natural estrogen by administration of natural and synthetic estrogens. In particular, for prophylactic purposes, calcium doses of approx. 1 gram of calcium per day are applied in man and woman.

Administration of estrogens such as, e.g., 17β-estradiol or the chemical derivatives thereof is, however, accompanied by the known grave side effects of uterotrophic effect, increased risk of thrombo-embolism, weight gain, and the like.

There have been many attempts reported in the prior art to find medicaments capable of producing an estrogen-type effect either without undesireable side effects, or with strongly diminished undesirable side effects. Plant extracts have been frequently used that exhibit the desired action of osteoporosis prophylaxis, but not, however, the undesirable uterotrophic effects.

Thus, for example, WO 99/47149 (=EP 1064009A1) to the present applicant discloses that extracts from iridaceae, in particular from _Cimicifuga racemosa_ and _Belamcanda chinensis_ and of the isoflavonoid tectorigenin contained therein, do not have an estrogen-type effect on the uterus, yet do so in the hypothalamo-hypophysary axis, in the cardiovascular system, and in the bone, so that these plant extracts may be employed for the prophylaxis and therapy of osteoporosis.

Moreover, calcium preparations for the prophylaxis of osteoporosis are known in the prior art. A pharmaceutical formulation to this end, besides an injection solution, is preferably an effervescent tablet for oral application. Such effervescent tablets may, e.g., have the following composition:

Tablets with 500 mg of Ca2+: 1250 mg of calcium carbonate, 2050 mg of citric acid, further constituents: lactose 1H2O, macrogol 6000, Povidon, sodium cyclamate, saccharine sodium 2H2O, Dimeticon 350, highly dispersed silica, macrogol stearate 400, sorbic acid, flavoring agents.

Tablets with 1000 mg of Ca2+: 4954 mg of calcium lactogluconate, 900 mg of calcium carbonate, and further constituents: citric acid, sodium cyclamate, saccharine sodium, mannitol, macrogol 4000, sodium hydrogencarbonate, flavoring agents.

In order to spare patients multiple applications, and also for cost reasons, a combination of calcium preparations having a high $Ca^{2+}$ content with dry plant extract having an anti-osteoporosis effect would be desirable.

Simple admixture to a calcium effervescent tablet mass, however, is foiled by the high sensitivity of the dry extracts to acids in an aqueous medium on the one hand, and by the poor water solubility of many dry extracts in an acidic medium on the other hand. Moreover the humidity-sensitive effervescent masses are imperiled by the highly hygroscopic dry extracts.

Encapsulation in customary gelatin capsules must equally be ruled out as the capsules are generally not water vapor tight and thus would decompose and/or agglomerate the dry plant extract, so that the pharmaceutical quality would cease to be ensured due to undefined bioavailability, release, and/or effectivity. Moreover the stability of such gelatin capsules is not warranted, for it is reported in literature, e.g., that instances of crosslinking with the gelatin occur when plant extracts are encapsulated in gelatin, and significant changes of the ingredients result from water absorption by the dry extract.

Thus, for example, a sugar-coated tablet, or dragée, formulation consisting of a mixture of calcium and dry plant extract would be optimal. As was mentioned above, significant calcium contents of 500 mg $Ca^{2+}$ and more, together with the relatively large amounts of auxiliaries for dragée manufacture, would result in large dragée sizes and weights which would not be acceptable to patients.

Known solid formulations are combination preparations of calcium with vitamin D3 in the form of chewing tablets, e.g. as Ossofortin® forte chewing tablets by the company Strathmann AG+Co., Sellhopsweg 1, D-22459 Hamburg.

Such chewing tablets for supportive treatment of osteoporosis have the following composition:

1500.3 mg of calcium carbonate (corresponding to 600 mg of Ca++), Colecalciferol dry concentrate (100 000 I.U./g) 400 I.U., further constituents: xylitol, corn starch, saccharine sodium, flavoring agent, magnesium stearate.

Up to the present, no prior art has taught the combination of calcium preparations with plant extracts suited for the above described prophylaxis and/or therapy of osteoporosis, for the above named reasons.

SUMMARY OF THE INVENTION

Accordingly it is an object of the present invention to furnish a pharmaceutical formulation combining both the advantages of calcium substitution and—where necessary—vitamin $D_3$ substitution, and the advantages of a dry plant extract for the prophylaxis and/or treatment of osteoporosis.

This object is attained through a pharmaceutical formulation in the form of a coated tablet, wherein the coating is a pressed body of at least one calcium salt, and the core is a pressed body of at least one of the named dry plant extracts, wherein vitamin $D_3$ may in addition be contained in the core.

The invention in particular concerns a pharmaceutical formulation of a calcium salt and a dry plant extract, wherein the pharmaceutical formulation includes an inner pressed body of at least one dry plant extract enveloped by at least one coating of at least one calcium salt.

Through the pharmaceutical formulation of the invention it is possible for the first time to furnish combinations that are sensible in terms of quantities, of dry plant extracts effective against osteoporosis, such as, for example, *Cimicifuga racemosa, Belamcanda chinensis, Vitex agnus castus* or *Urtica dioica radix*, and their mixtures, with calcium. Here it is particularly advantageous that the coating—other than customary in the prior art—consists of auxiliaries, but essentially contains active agent, i.e, calcium, exclusively.

DETAILED DESCRIPTION

For the manufacture of the dry plant extracts, the present applicant's PCT application WO 99/47149 is incorporated in its entirety by reference. In addition to the solvents mentioned there, however, it is furthermore possible to extract the plants in question with mixtures of organic-aqueous solvents, exclusively aqueous, or also with the aid of supercritical $CO_2$ (e.g. in the case of *Serenoa repens*).

By the present pharmaceutical formulation it is achieved that the generally highly hygroscopic plant extracts usually formulated by addition of water-binding auxiliaries e.g. to dragées or film tablets, may be made available with a low mass and small volume, embedded in a coat of an inert active principle having a protective effect against humidity in the form of a calcium salt.

As a result, an extremely favorable ratio of dry plant extract to calcium to auxiliaries is obtained, so that it is partly even possible to entirely omit auxiliaries, with the exception of small amounts of lubricants.

Thus it is for the first time possible to furnish a combination preparation of a dry plant extract, calcium salts and—where necessary—also vitamin $D_3$, which has a calcium content whereby the approximately 1000 mg of $Ca^{2+}$ ions p.d. required for prophylaxis and/or therapy may be achieved without administration of additional calcium preparations.

A preferred embodiment of the present invention is characterized in that in the calcium-containing coating and/or in the inner dry plant extract pressed body it additionally contains cholecalciferols, in particular Colecalciferol (vitamin D3).

Moreover the pharmaceutical formulation may in addition contain at least one fluoride salt, in particular sodium fluoride, wherein it is preferred for the fluoride salt to be present in the inner pressed body.

Preferably the pharmaceutical formulation is characterized in that the dry plant extract is selected from the group consisting of extracts from: *Vitex agnus castus* (chaste tree); *Belamcanda chinensis* (leopard lily/blackberry lily); *Cimicifuga racemosa* (black cohosh); *Trifolium pratense L.* (purple trefoil); *Oenothera biennis hom.* (primrose); *Glycine soja* (soy bean); *Serenoa repens* (saw-palmetto); *Urtica dioica* (stinging nettle), in particular its root; *Cucurbita pepo* (pumpkin), in particular its seed; *Pygeum africanum*; as well as suitable mixtures of these.

In a preferred embodiment of the pharmaceutical formulation of the invention, the calcium salt is selected from the group consisting of calcium carbonates; calcium hydrogen carbonates; calcium halides, in particular calcium chlorides and calcium iodides; calcium phosphates; calcium hydrogen phosphates, in particular calcium monohydrogen phosphate; dicalcium hydrogen phosphates, calcium lactates; calcium lactonates; calcium succinates; calcium tartrates; calcium gluconates; others; as well as suitable mixtures of the above.

The preferred pharmaceutical formulation in accordance with the present invention is a coated tablet, wherein the coating is a pressed body of at least one calcium salt, and the core is a pressed body of at least one of the named dry plant extracts, wherein vitamin $D_3$ may in addition be contained in the core.

The pharmaceutical formulation may, however, also be a dot tablet (bull-eye tablet) in which the core, although still entirely enveloped by the coating, nevertheless need not be centered inside the coating.

It is furthermore possible in the present pharmaceutical formulation to form the coating of a plurality of calcium layers, wherein preferably each layer contains a different calcium salt.

A preferred pharmaceutical formulation has, e.g., a calcium content of approx. 50 to 1000 mg per coated tablet and a dry plant extract content of approx. 0.5 to 100 mg. Hereby it is possible through one to three administrations per day, which is agreeable for the patient, to supply the entire recommended daily dose of $Ca^{2+}$ ions of approx. 1000 mg of $Ca^{2+}$ with simultaneous administration of the required phytoextracts having an anti-osteoporosis action and of vitamin $D_3$.

Moreover a preferred pharmaceutical formulation may have a polymer film as an external envelope, whereby the swallowing property and the esophageal sliding property may be improved. Moreover the polymer film may prevent dust abrasion and the penetration of humidity into the coating. Such a polymer envelope is, however, not essential.

The pharmaceutical formulation of the present invention requires few auxiliaries or even none at all. Where necessary, however, the auxiliaries customary in galenics, for example disintegrants, in particular on the basis of starches and/or their derivatives; binders, in particular microcrystalline cellulose, gum arabic; lubricants, in particular stearic acid and/or magnesium stearate; as well as slip agents, in particular polyethylene glycol, and the like may be used.

Preferably the pharmaceutical formulations of the invention are suited as medicaments for the treatment of osteoporosis of various geneses, and in a particularly preferred manner for the prophylaxis and/or therapy of osteoporoses brought about by lack of sexual hormone in women and men of advanced age.

Manufacture of the pharmaceutical formulations of the invention takes place in accordance with the following principle:

Initially a pressed body core is produced from a dry plant extract, wherein the dry plant extract is selected from the group consisting of: *Vitex agnus castus* (chaste tree); *Belamcanda chinensis* (leopard lily); *Cimicifuga racemosa* (black cohosh); *Trifolium pratense L.* (purple trefoil); *Oenothera biennis hom.* (primrose); *Glycine soja* (soy bean); *Serenoa repens* (saw-palmetto); *Urtica dioica* (stinging nettle), in particular its root; *Cucurbita pepo* (pumpkin), in particular its seed; *Pygeum africanum*; as well as suitable mixtures of these.

This core is transferred onto a first partial quantity of a coating mixture of at least one calcium salt, subsequently filling is performed with a second partial quantity of the coating mixture; and the entire formulation of the core and the two partial quantities of calcium salt-containing coating mixture is pressed to form the pharmaceutical formulation. The calcium salt is selected from the group consisting of:

calcium carbonates; calcium hydrogen carbonates; calcium halides, in particular calcium chlorides and calcium iodides; calcium phosphates; calcium hydrogen phosphates, in particular calcium monohydrogen phosphate; dicalcium hydrogen phosphates, calcium lactates; calcium lactonates; calcium succinates; calcium tartrates; calcium gluconates; others; as well as suitable mixtures of these.

Preferably the core is substantially centered on the first partial quantity of the coating mixture, whereby a so-called coated tablet is obtained. It is, however, also possible to manufacture so-called bull-eye-tablets (dot tablets) having a core which is not centered, however enveloped, and in which the core may be partly visible through the coating.

For pressing tablets, commercially available tablet presses may be used, such as those of the companies FETTE, KORSCH and KILIAN. Particularly suited, for example, is a synchronously operating double-sided rotary press by the company MANESTY. In the double-sided rotary press, the cores are produced on the one tower of the rotary press and transferred by the intermediate transferring and centering mechanism to the tower of the second rotary press, where press-application of the coating takes place.

More basically, the pharmaceutical formulations of the present invention may, however, also be carried out with two rotary presses, where the cores are pressed in one of them, while press-application of the coating takes place in the second one.

The advantage for the manufacture of the coated tablets of the invention as a pharmaceutical formulation with the aid of a double-sided rotary press, however, resides in the fact that the cores may be pre-pressed in the first tower of the press so as to be comparatively soft. Final compression in the second tower of the double-sided rotary press thus results in very good adhesion between dry plant extract core and calcium coating.

A coated tablet manufactured in this manner has, for example, the following composition:

| Coating: | $CaCO_3$ | 1250 mg (corr. to 500 mg of $Ca^{2+}$) |
|---|---|---|
| | vitamin $D_3$ | 200 I.U. |
| Core: | *Cimicifuga racemosa* (dry extract preparation) | 20 mg |
| Auxiliaries: | magnesium stearate | 8 mg |
| | stearic acid | 4 mg |
| | microcrystalline cellulose | 40 mg |
| | gum arabic | 50 mg |

The exemplary coated tablet combines the advantages of oral calcium and vitamin $D_3$ substitution with the required dose of *Cimicifuga racemosa* dry extract. By oral application of no more than 2 tablets daily, the dose recommended for the prophylaxis and/or therapy of osteoporosis of calcium and vitamin $D_3$ dose of approx. 1000 mg of $Ca^{2+}$ p.d., or 400 I.U. of vitamin $D_3$, as well as the desired simultaneous administration of 40 mg of *Cimicifuga racemosa* dry extract is achieved.

It is, of course, also possible and advantageous to manufacture the dry extract core from other of the named phyto-extracts or from mixtures of different extracts depending on the constellation of indications. Thus, e.g., a coated tablet of the invention, adjusted for ailments of the prostate, may contain a *Serenoa repens* extract in the core.

The invention claimed is:

1. A pharmaceutical tablet or dragée for the therapy of osteoporosis comprising:
   a.) an inner pressed body, said inner pressed body comprising at least one plant extract in dry form, said plant extract having an anti-osteoporosis effect, yet not having an estrogen type effect on the uterus, wherein said plant extract is selected from the group consisting of extracts from: *Vitex agnus castus* (chaste tree), *Belamcanda chinensis* (leopard lily), *Cimicifuga racemosa* (black cohosh); *Trifolium pratense L.* (purple trefoil), *Oenothera biennis hom.* (primrose), *Glycine soja* (soy bean), *Serenoa repens* (saw-palmetto), *Urtica dioica* (stinging nettle), *Cucurbita pepo* (pumpkin), *Pygeum africanum*, and suitable mixtures thereof, and
   b.) at least one coating enveloping said pressed body, said at least one coating consisting essentially of at least one calcium salt,
   wherein said dry plant extract and said calcium salt are present in sufficient amounts that when administered to a patient they cooperate for the therapy of osteoporosis.

2. The pharmaceutical tablet or dragée in accordance with claim 1, wherein the calcium salt is selected from the group consisting of: calcium carbonates, calcium hydrogen carbonates, calcium halides, calcium phosphates, calcium hydrogen phosphates, dicalcium hydrogen phosphates, calcium lactates, calcium lactonates, calcium succinates, calcium tartrates, calcium gluconates, and suitable mixtures thereof.

3. The pharmaceutical tablet or dragée in accordance with claim 1, wherein said calcium-containing coating and/or said inner pressed body of plant extract in dry form formulation further comprises one or more cholecalciferols.

4. The pharmaceutical tablet or dragée of claim 1, wherein said coating effectively protects the inner body from humidity.

5. A pharmaceutical tablet or dragée for the therapy of osteoporosis comprising:
   a.) an inner pressed body, said inner pressed body comprising 0.5 to 100 mg of at least one plant extract in dry form, said plant extract having an anti-osteoporosis effect, yet not having an estrogen type effect on the uterus, wherein said plant extract is selected from the group consisting of extracts from: *Vitex agnus castus* (chaste tree), *Belamcanda chinensis* (leopard lily), *Cimicifuga racemosa* (black cohosh); *Trifolium pratense L.* (purple trefoil), *Oenothera biennis hom.* (primrose), *Glycine soja* (soy bean), *Serenoa repens* (saw-palmetto), *Urtica dioica* (stinging nettle), *Cucurbita pepo* (pumpkin), *Pygeum africanum*, and suitable mixtures thereof, and
   b.) at least one coating enveloping said pressed body said at least one coating consisting essentially of at least one calcium salt, said calcium salt present in an amount to provide from approx. 50 to 1000 mg calcium per coated tablet,
   whereby said dry plant extract and said calcium salt are present in sufficient amounts that when administered to a patient they cooperate for the therapy of osteoporosis.

* * * * *